Figure 1:
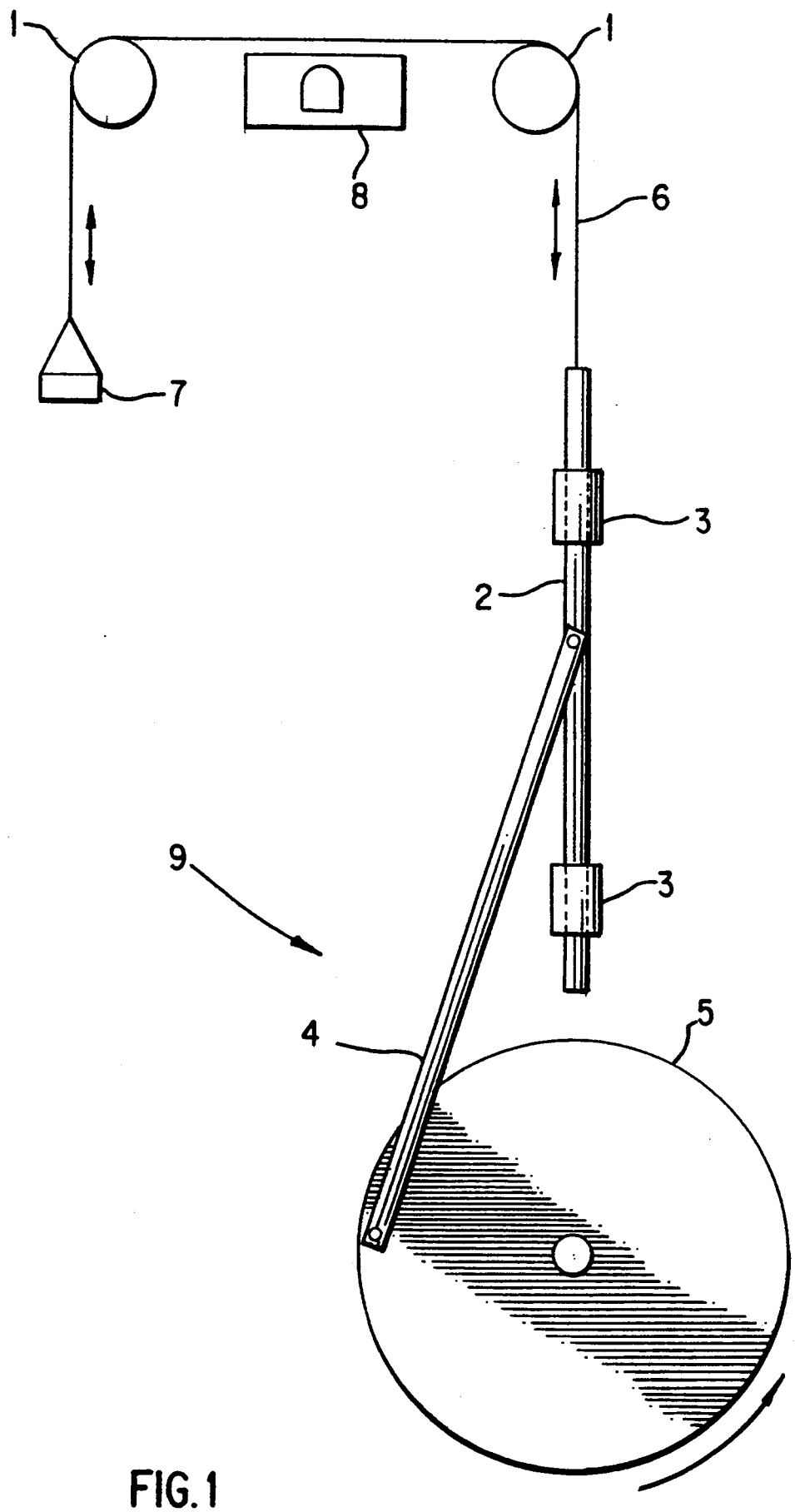

United States Patent [19]

Dasgupta et al.

[11] Patent Number: 5,341,103
[45] Date of Patent: Aug. 23, 1994

[54] APPARATUS FOR SIMULTANEOUSLY GENERATING AND MEASURING A TRIBOELECTRIC CHARGE

[75] Inventors: Sunil P. Dasgupta; Blain H. Gingrich, both of Wilmington; Bernard J. Matyniak, New Castle; G. Gregory Weaver, Hockessin, all of Del.

[73] Assignee: Hercules Incorporated, Wilmington, Del.

[21] Appl. No.: 894,327

[22] Filed: Jun. 4, 1992

[51] Int. Cl.$^5$ .............................................. G01N 27/60
[52] U.S. Cl. .................................................... 324/454
[58] Field of Search ............... 324/452, 454, 457, 71.1; 73/159, 160; 340/677; 310/308–310

[56] References Cited

U.S. PATENT DOCUMENTS

| | | | |
|---|---|---|---|
| 2,421,430 | 6/1947 | Ott | 175/183 |
| 2,663,842 | 12/1953 | Graham | 324/454 |
| 3,246,239 | 4/1966 | Olney | 324/454 X |
| 3,364,423 | 1/1968 | Moulton | 324/454 X |
| 3,487,296 | 12/1969 | Frederick | 324/454 |
| 3,733,544 | 5/1973 | Petrick et al. | 324/454 |
| 3,859,593 | 1/1975 | Poole | 324/454 |
| 4,677,387 | 6/1987 | Mutter et al. | 324/454 |
| 4,885,543 | 12/1989 | Smith | 324/452 |
| 4,983,923 | 1/1991 | Taniguchi | 324/454 |

FOREIGN PATENT DOCUMENTS 925319 2/1955 Fed. Rep. of Germany .
1568966 6/1980 United Kingdom .

OTHER PUBLICATIONS

Journal of Physics E; Scientific Instruments, vol. 9, No. 3, Mar. 31, 1976, pp. 226–229, K. Ohara, "Apparatus For Simultaneous Measurements of Static Electricity and Friction of Polymer Films".

Primary Examiner—Gerard R. Strecker
Assistant Examiner—Warren S. Edmonds
Attorney, Agent, or Firm—Roy V. Jackson; Ivan G. Szanto

[57] ABSTRACT

Apparatus for simultaneously generating and measuring a triboelectric charge generated on a strip of flexible sample material includes a stationary rod of insulating material, driving motor for the sample material adapted to move the sample material in frictional contact with the rod, a support rod for maintaining a surface of the sample material in straight-line tangential relationship with the rod, and a static-charge sensor disposed between the stationary rod and the support rod and spaced from the surface of the sample material for measuring a charge on the surface in cooperation with a voltage-measuring device.

3 Claims, 2 Drawing Sheets

APPARATUS FOR SIMULTANEOUSLY GENERATING AND MEASURING A TRIBOELECTRIC CHARGE

The present invention relates to the measurement of a triboelectric charge generated on a surface. In particular it relates to measurement of a generated charge on surfaces such as paper, film, or fabric.

Owing to the nature of many paper, film, and fabric surfaces, an electric charge can be generated on these surfaces when they rub against another surface. Furthermore many additives to such materials, such as fillers and sizes in paper manufacture, can alter the surface properties of such materials and thereby, affect the electric charge generated. This electric charge, known as the "triboelectric charge," can have important implications with respect to operations performed on these materials to make end-use products.

The amount of the triboelectric charge that is generated during the movement of paper, film, or fabric surface can adversely affect the running of operations on the material. For example, in the manufacture of paper products, this triboelectric charge becomes very important for converting, printing, duplicating, and preparing stationary products such as envelops. During such processes, the paper surface moves against another dissimilar surface, and the friction caused can result in the generation of a triboelectric charge on the paper. When the triboelectric charge on the moving paper surface becomes relatively high, serious interference with the normal conditions of the operation process takes place.

Compositions known as "antistats" are added to certain materials to control the generation of a triboelectric charge on the surface of the material during processing operations. For various reasons, it is useful to know the amount of the triboelectric charge that can be generated on a material surface, for example, to determine the amount of antistat needed to control it. Techniques are known for sequentially effecting a triboelectric charge on a surface, and then measuring the amount of the charge thereby generated.

According to the present invention, an apparatus for simultaneously generating and measuring a triboelectric charge generated on an elongated strip of flexible sample material, comprises a stationary rod of insulating material fixedly attached to the apparatus, driving means including a motor for the sample material and adapted to move the ample material longitudinally in transverse frictional contact with the rod, means for maintaining the sample material under continuous tension, support means for maintaining a surface of the sample material in substantially straight-line tangential relationship with the rod after it leaves contact with it, and a static-charge sensor disposed between the stationary rod and the said support means and spaced from the said surface of the sample material for measuring, in cooperation with electrically associated voltage-measuring means, a charge on the said surface.

Preferably the driving means for the sample material is a reciprocating arm for connection to one end of the sample material and driven by the motor through a rotating axle, and the support means is a second stationary rod of insulating material spaced from the said stationary rod, the means for maintaining the sample material under continuous tension being a tensioning weight adapted to be attached to the other end of the sample material, the two stationary rods being spaced from the reciprocating arm by at least the extent of the reciprocation, the reciprocating arm being attached to a drive axle at a point spaced from its axis of rotation to provide a cranking function.

According to an alternative version of the invention, the sample material extends in a closed loop around the stationary rod and a parallel rotatable rod spaced from the stationary rod to provide the said support means, the sample material being in frictional contact with both the rods, and driving means for to the sample material includes a drive pulley driven by the motor to rotate the rotatable rod and an idler pulley rotatable on a non-rotating shaft axially connected to the stationary rod, and the means for maintaining the sample material under continuous tension being a spring connected to the idler pulley and biasing it away from the drive pulley to exert tensioning force on the loop of sample material.

Figure 2:
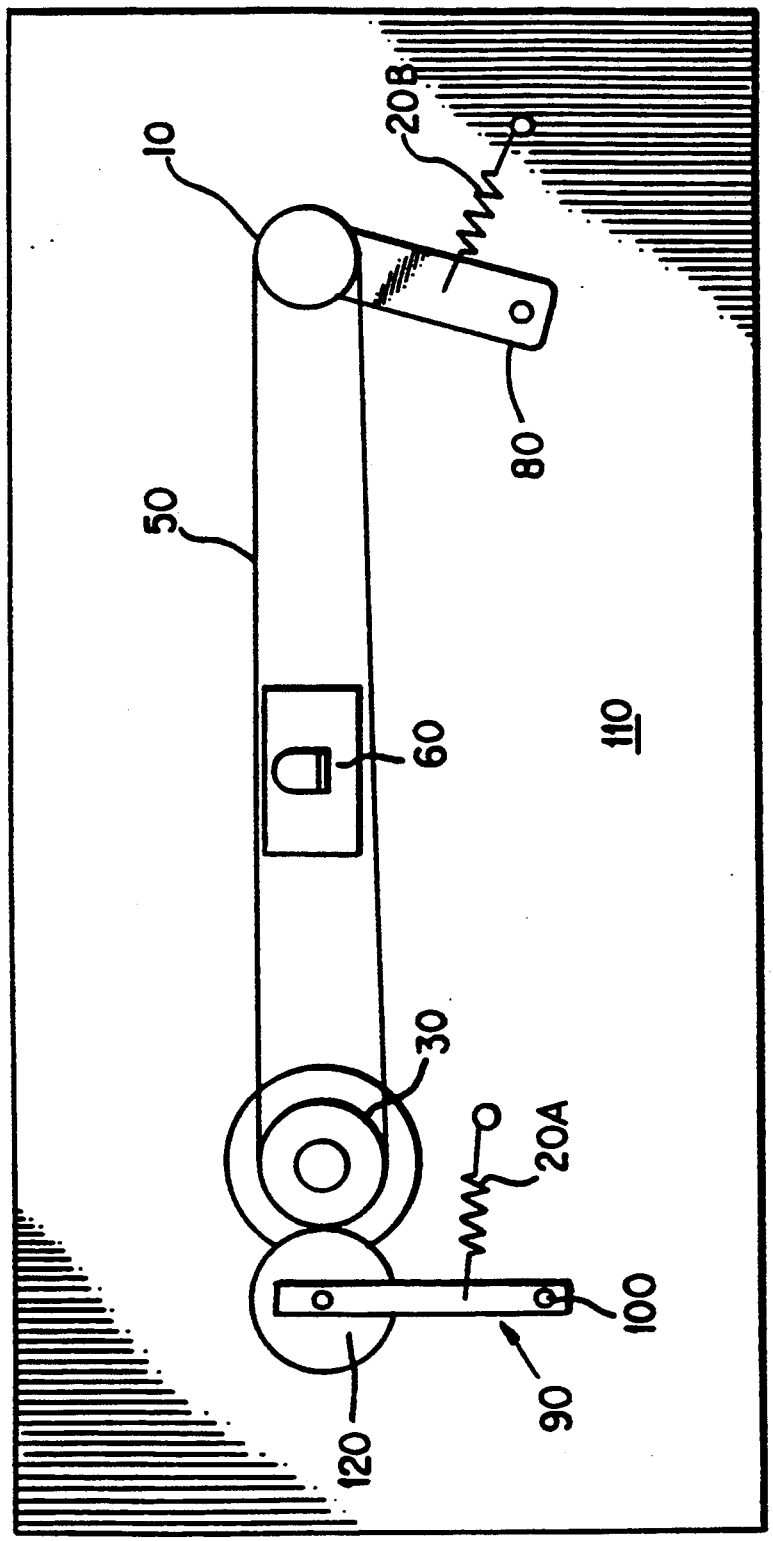

FIGS. 1 and 2 are plan views of alternative preferred embodiments of the present invention.

With reference to FIG. 1, two stationary insulated rods 1 for rubbing the sample material 6 are attached to a metal panel 9 along with bearing assembly 3, drive wheel 5, and static charge sensor 8. The insulated rods are made of flexible material such as polytetrafluoroethylene or other insulating material that is preferably capable of consistently generating a desirable amount of a triboelectric charge on the surface of the rubbed material. The sample material is attached to a connecting rod 2, which extends to the drive rod 4 through linear bearing assemble 3. Preferably, the drive rod is made of a sturdy lightweight material such as aluminum and the bearing is made of a low friction material requiring no lubrication such as polypropylene. The drive wheel 5 is connected to a variable speed motor (not shown), which controls the movement of the test sample 1 and the speed of the rubbing process. A weight 7 is attached to the other end of the sample material 6 to provide sufficient tension on the sample material and maintain its uniform movement. Sufficient tension is necessary to keep the surface of the sample uniformly flat across the top of the insulating rods and maintain a uniformly constant distance between the sample surface and the static charge sensor. Static-charge sensor 8, such as Detector/Preamplifier Probe, Model 1025 (available from Monroe Electronics Inc., New York) is attached to the panel 9 such that it maintains a desirable distance from the sample during the rubbing process. Since the distance between the sensor and the sample controls the level of output from the sensor, the distance is selected so as to result in accurate and reproducible data. Preferably, the distance is 0,025–0.075 inches (0.0635–0.1905 cm), more preferably 0.050 inches (0.127 cm), for fabrics and 0.1–0.2 inches (0.254–0.508 cm), more preferably 0.125 inches (0.3175 cm), for fibers. The output from the sensor 8 is fed into an electrostatic voltmeter (not shown), and the voltmeter output is fed into a recorder (not shown) for printing the triboelectric charge characteristics. An exemplary voltmeter is the ISOPROBE Electrostatic Voltmeter, Model 260 (available from Monroe Electronics Inc.), and a suitable recorder is the LR 4100, Model 3711 (available from Yokogawa Electric Corp., Georgia). As the surface charge is generated by rubbinq the sample against the rods, the charge is measured by the volt meter and recorded on the recorder. In addition to measuring the charge simultaneously with its generation, after generating the surface charge and discontinuing the charge-generation (rubbing) process, the discharge or decay characteristics of the generated surface charge can also be measured and recorded. Materials whose surface charge quickly dissipates will cause significantly fewer problems during manufacturing operations than those that retain their surface charge longer.

With reference to FIG. 2, a stationary insulating rod 10 of a suitable material as described hereinabove is attached to metal panel 110 along with tensioning springs 20A, drive pulley 30, idle pulley 120, and static-charge sensor 60. The sample material 50 is in the form of a continuous loop or belt mounted over the stationary rod 10 and drive pulley 30, also made of a chosen material and insulated from the panel 110. Pulley 30 is driven by a variable speed motor (not Shown). One tensioning spring 20B is biased against lever 80 connected to stationary rod 10 to maintain a desired tension on the sample material 50. The other tensioning spring 20A is biased against lever 90 connected to idler pulley 120 to provide additional tension on sample material 50. If additional tension is not desired, idler pulley 120 can be moved away from the sample and fixed in this position by tightening screw 100. Static charge sensor 60 is located between the belt of material 50, about midway between drive pulley 30 and stationary rod 10. Measuring triboelectric charge and evaluation of charge decay characteristics are as described for the embodiment provided in FIG. 1.

In order to more clearly describe the present invention, the following non-limiting examples are provided. In the following examples, all parts and percentages are by weight unless indicated otherwise.

EXAMPLE 1

Using the embodiment described in FIG. 1, the triboelectric charge is measured on samples of commercially available alkaline sized paper while rubbing at a speed of 266.7 cm/min. Two types of alkaline sized paper are used, one containing an antistat of sodium chloride (1 part sodium chloride per 500 parts paper), and the other containing no antistat. The stable charge measured on the surface of the sodium chloride-treated paper is 132 volts and on the surface of the non-treated paper is 438 volts.

EXAMPLE 2

Samples of paper as in Example 1 are tested using the embodiment described in FIG. 2 at a rubbing speed of 254 cm/min. The stable charge generated on the surface of the sodium chloride-treated paper is 65 volts and on the surface of the non-treated paper is 310 volts.

We claim:

1. Apparatus for simultaneously generating and measuring a triboelectric charge generated on an elongated strip of flexible sample material comprises a stationary rod of insulating material fixedly attached to the apparatus, driving means including a motor for the sample material and adapted to move the sample material longitudinally in transverse frictional contact with the rod, means for maintaining the sample material under continuous tension, support means for maintaining a surface of the sample material in substantially straight-line tangential relationship with the rod after it leaves contact with it, and a static-charge sensor disposed between the stationary rod and the said support means and spaced from the said surface of the sample material for measuring, in cooperation with electrically associated voltage-measuring means, a charge on the said surface.

2. Apparatus for simultaneously generating and measuring a triboelectric charge as claimed in claim 1, in which the driving means for the sample material is a reciprocating arm for connection to one end of the sample material and driven by the motor through a rotating axle, and the support means is a second stationary rod of insulating material spaced from the said stationary rod, the means for maintaining the sample material under continuous tension being a tensioning weight adapted to be attached to the other end of the sample material, the two stationary rods being spaced from the reciprocating arm by at least the extent of the reciprocation, and the reciprocating arm being attached to a drive axle at a point spaced from its axis of rotation to provide a cranking function.

3. Apparatus for simultaneously generating and measuring a triboelectric charge as claimed in claim 1, in which the sample material extends in a closed loop around the stationary rod and a parallel rotatable rod spaced from the stationary rod to provide the said support means, the sample material being in frictional contact with both the rods, the driving means for the sample material includes a drive pulley driven by the motor to rotate the rotatable rod and an idler pulley rotatable on a non-rotating shaft axially connected to the stationary rod, and the means for maintaining the sample material under continuous tension being a spring connected to the idler pulley and biasing it away from the drive pulley to exert tensioning force on the loop of sample material.

* * * * *